(12) United States Patent
Goto

(10) Patent No.: US 11,369,493 B2
(45) Date of Patent: Jun. 28, 2022

(54) KNEE JOINT COMPONENT, KNEE JOINT AND ARTIFICIAL LEG

(71) Applicant: IMASEN ENGINEERING CORPORATION, Gifu (JP)

(72) Inventor: Manabu Goto, Gifu (JP)

(73) Assignee: IMASEN ENGINEERING CORPORATION, Gifu (JP)

( * ) Notice: Subject to any disclaimer, the term of this patent is extended or adjusted under 35 U.S.C. 154(b) by 0 days.

(21) Appl. No.: 17/054,517

(22) PCT Filed: May 13, 2019

(86) PCT No.: PCT/JP2019/018858
§ 371 (c)(1),
(2) Date: Nov. 10, 2020

(87) PCT Pub. No.: WO2019/221037
PCT Pub. Date: Nov. 21, 2019

(65) Prior Publication Data
US 2021/0186713 A1 Jun. 24, 2021

(30) Foreign Application Priority Data

May 14, 2018 (JP) .............................. JP2018-092712

(51) Int. Cl.
*A61F 2/64* (2006.01)
*A61F 2/68* (2006.01)
(Continued)

(52) U.S. Cl.
CPC .................. *A61F 2/64* (2013.01); *A61F 2/68* (2013.01); *A61F 2/74* (2021.08); *A61F 2/80* (2013.01); *A61F 2002/5086* (2013.01)

(58) Field of Classification Search
CPC ....................................................... A61F 2/64
See application file for complete search history.

(56) References Cited

U.S. PATENT DOCUMENTS

2010/0191347 A1 * 7/2010 Pusch ....................... A61F 2/70
623/27
2015/0305895 A1 * 10/2015 Boiten ....................... A61F 2/64
623/26

FOREIGN PATENT DOCUMENTS

JP 2005331107 A * 12/2005 ............... F16F 9/466
JP 2014221093 A * 11/2014

* cited by examiner

*Primary Examiner* — Jerrah Edwards
*Assistant Examiner* — Ashley N. Coggins
(74) *Attorney, Agent, or Firm* — Hedman & Costigan, P.C.; James V. Costigan; Kathleen A. Costigan

(57) ABSTRACT

It is an object of the present invention to provide a technique capable of making a knee joint of an artificial leg close to a movement of a knee of a human body with a simple configuration. The knee joint component 4, which is one application example of the present invention, includes a first oil passage 20 connecting a first oil chamber 13a and a second oil chamber 13b in a cylinder tube 12 coupled to a socket 8 mounted on a thigh part 7, a second oil passage 30 branched from the first oil passage 20 so as to be in parallel with the first oil passage 20, and a switching mechanism 50 that switches whether a oil 19 passes through the first oil passage 20 or the second oil passage 30, which are different from the first oil passage 20 in the passage characteristics, and the switching mechanism 50 that is rotatably mounted around the first rotating shaft 53 and that is rotatable by its own weight when the artificial leg 9 is tilted, and a first rotating member 52 that switches whether the oil 19 passes through the first oil passage 20 or the second oil passage 30 by opening or closing the inlet/outlet 31,32 of the second oil passage 30.

4 Claims, 17 Drawing Sheets

(51) Int. Cl.
*A61F 2/80* (2006.01)
*A61F 2/50* (2006.01)
*A61F 2/74* (2006.01)

FIG.10
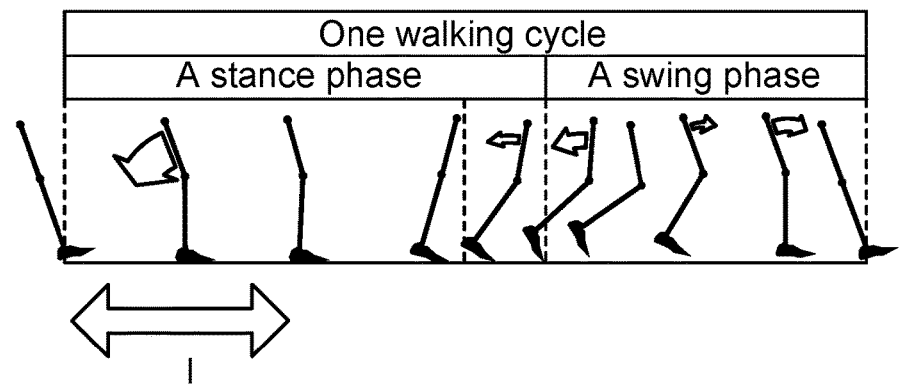
FIG.10A
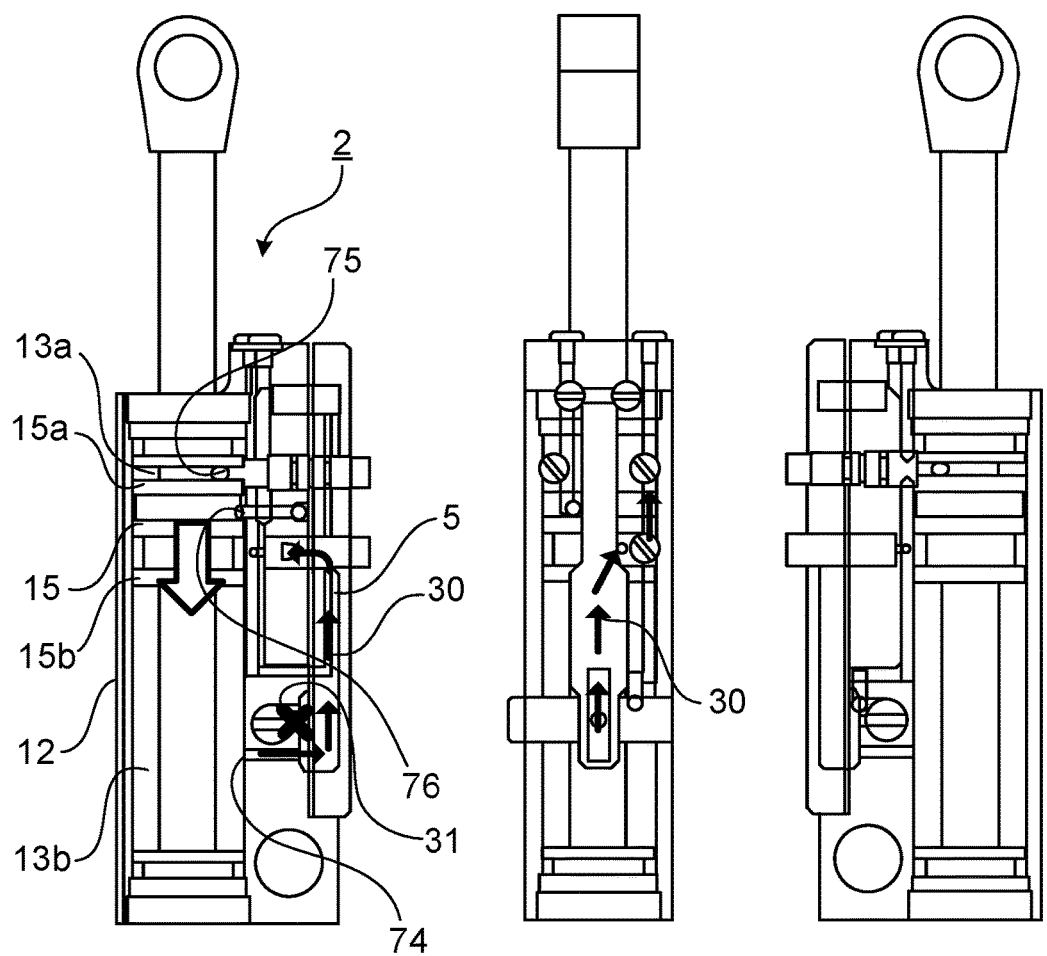
FIG.10B  FIG.10C  FIG.10D

FIG.11
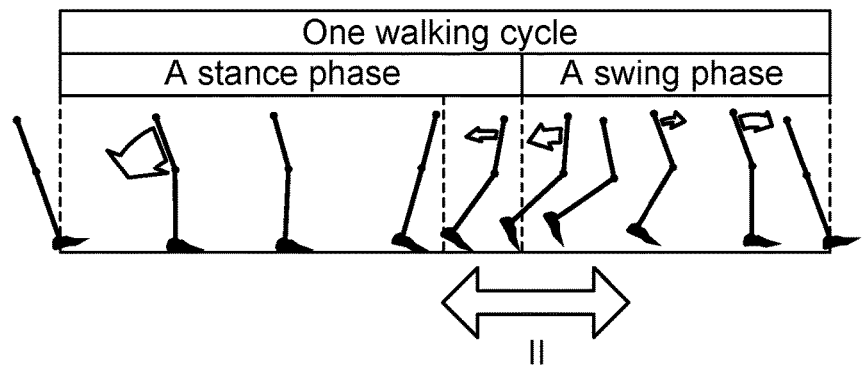
FIG.11A
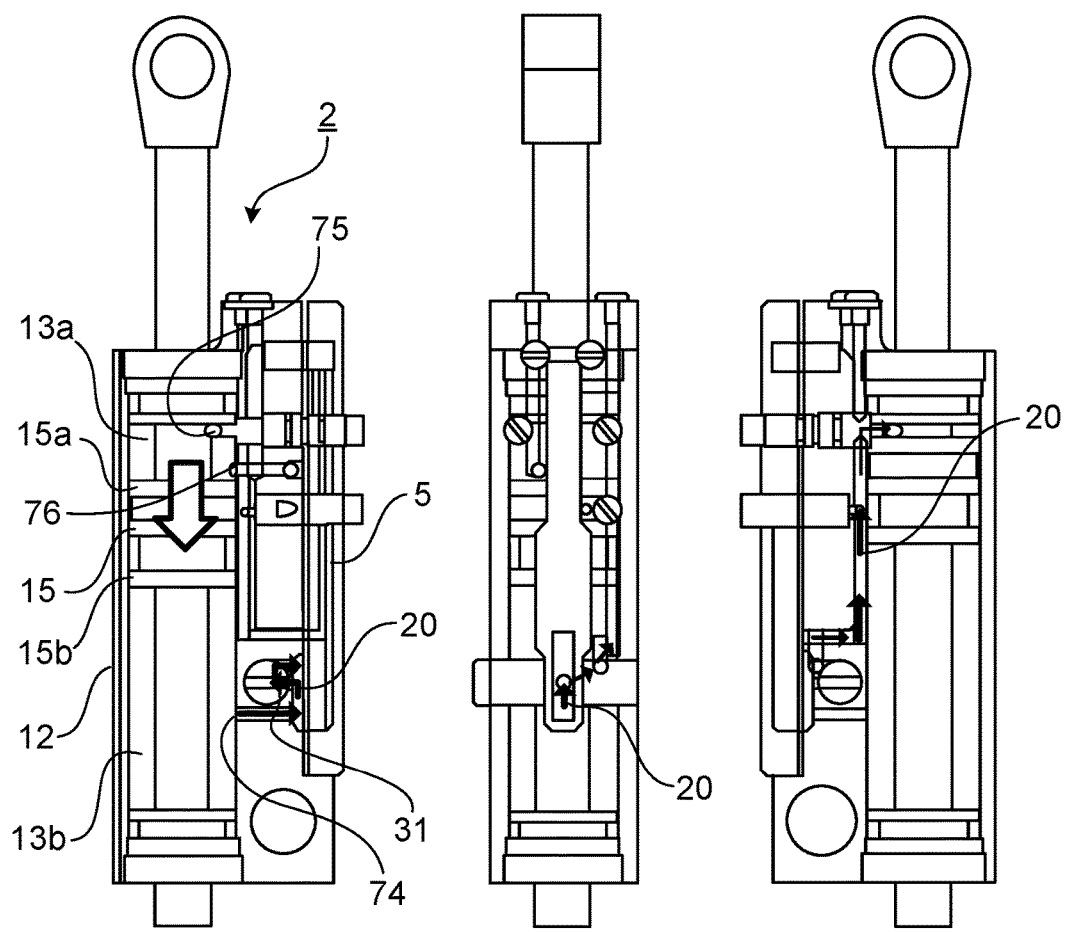
FIG.11B     FIG.11C     FIG.11D

FIG.12
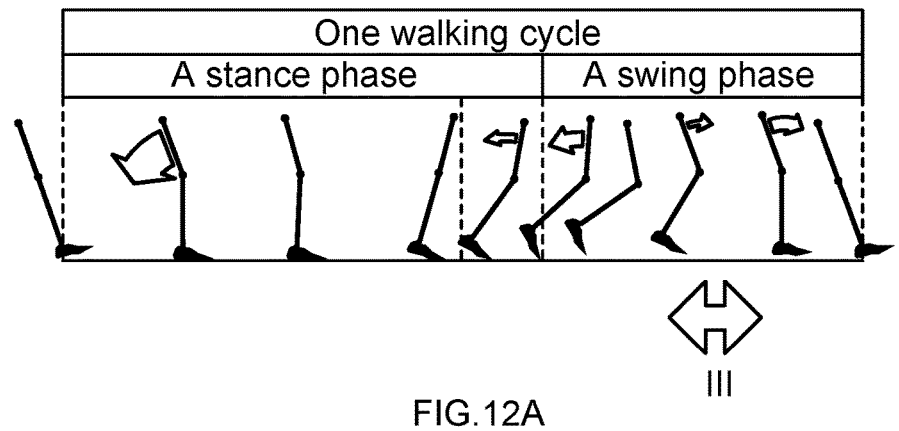
FIG.12A
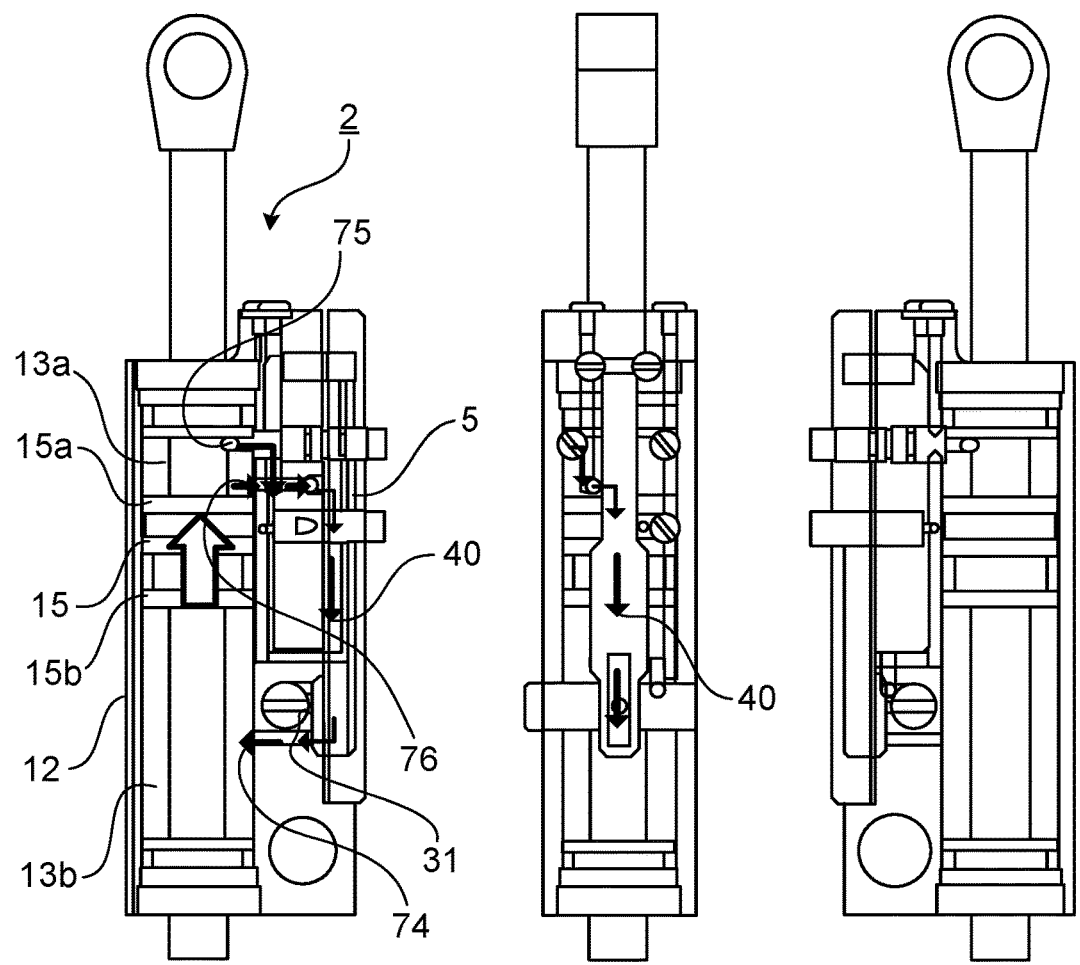
FIG.12B    FIG.12C    FIG.12D

FIG.13
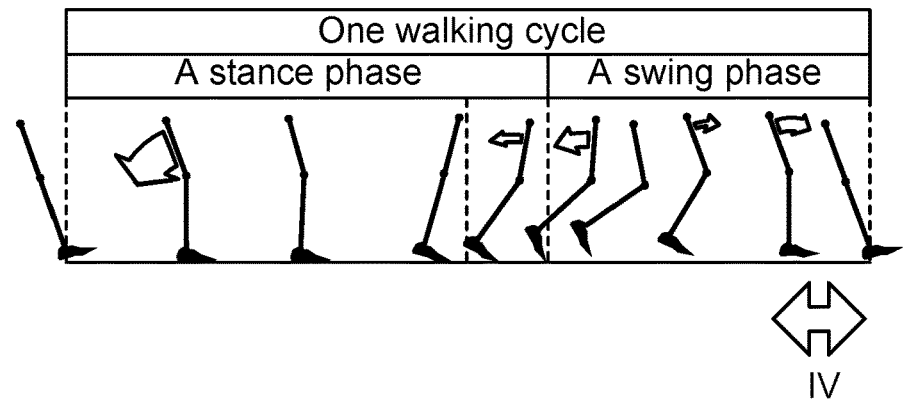
FIG.13A
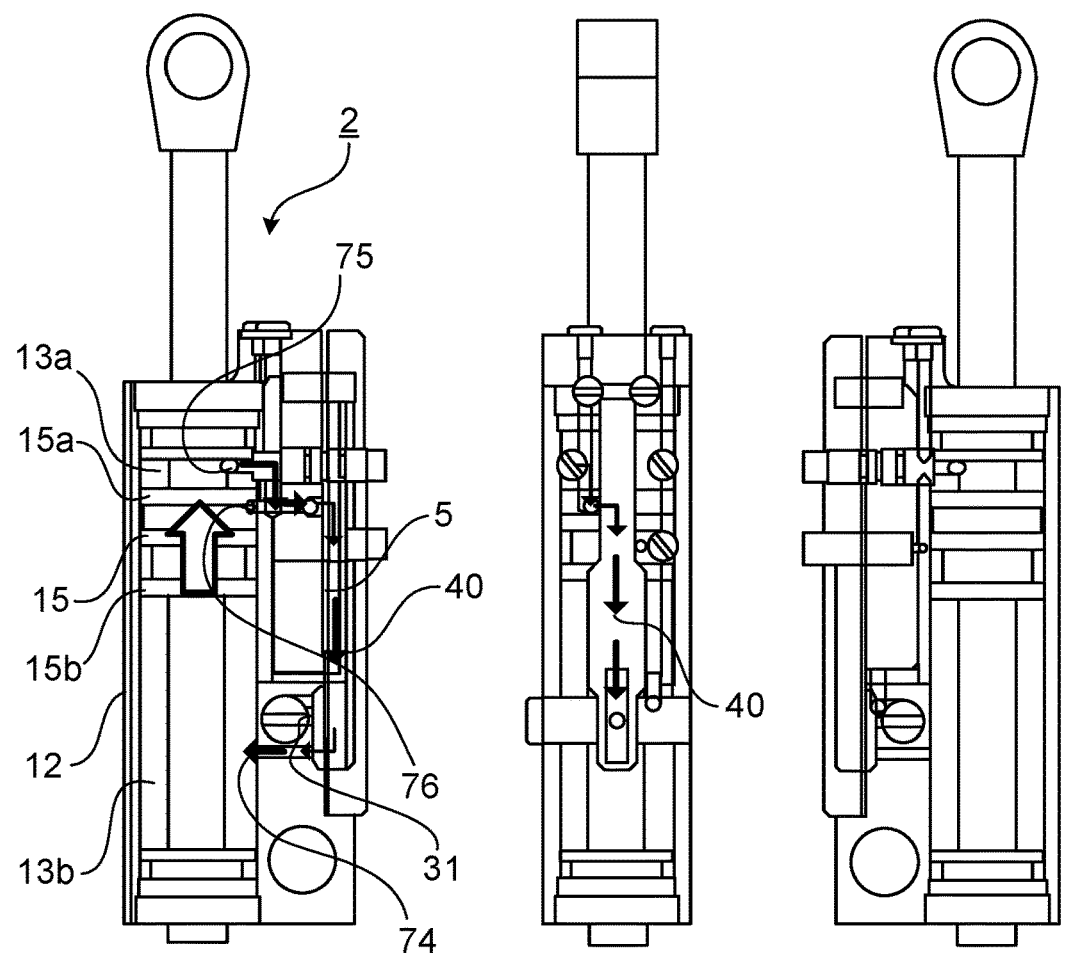
FIG.13B    FIG.13C    FIG.13D

| State | Figure 14,15 | Lever position | The bending resistance | |
|---|---|---|---|---|
| | | | Forward tilt | Backward tilt |
| Normal state | A | Lower | Weak | Strong |
| Free state | B | Central | Weak | Weak |
| Yield state | C | Upper | Strong | Strong |

KNEE JOINT COMPONENT, KNEE JOINT AND ARTIFICIAL LEG

TECHNICAL FIELD

The present invention relates to a knee joint component used for a knee portion of an artificial leg, a knee joint and an artificial leg using a knee joint.

BACKGROUND ART

Conventionally, there has been an artificial leg in which a first pressure sensor for detecting a weight load and a contraction motion of a muscle of a stump end of a cutting leg is provided on an inner surface of a femoral socket of an artificial leg attached to a stump end of a cutting leg, a second pressure sensor for mainly detecting a weight load is provided on a bottom surface of the femoral socket, and when a pressure of the first pressure sensor is higher than a pressure of the second pressure sensor by a predetermined pressure or more, a throttling state of a variable valve of a hydraulic cylinder for adjusting a resistance of flexion and extension of a knee joint portion is controlled by detection information of a pressure difference between the first pressure sensor and the second pressure sensor (for example, see Patent Document 1).

CITATION LIST

Patent Literature

PATENT LITERATURE 1: JP 2001-218778 A

SUMMARY OF INVENTION

Problems to be Solved by Invention

However, as in the above-mentioned artificial leg, in the artificial leg, a pressure sensor is disposed on the inner surface of the thigh socket portion and the bottom surface of the thigh socket, respectively, and the pressure detected by the pressure sensor is input to a control device to perform a comparison process, and based on the result, in the artificial leg controlling the hydraulic cylinder, there are many components, and electronic processing and control are necessary. That is, there is a problem that the structure and control are complicated.

The present invention has been made in view of such problems, and an object of the present invention is to provide a technique capable of making a knee joint of an artificial leg close to a movement of a knee of a human body with a simple configuration. The present invention has been made in order to solve at least a part of the above-mentioned problems, and can be realized as the following application example.

Solution to Problems

In this section, reference numerals in parentheses, supplementary explanations, and the like indicate corresponding relationships with embodiments described later in order to facilitate understanding of the present invention, and do not limit the present invention in any way.

Application Example 1

A knee joint component (4) according to the present invention is a knee joint component (4) to be mounted on a hydraulic cylinder (10) including, a cylinder tube (12) coupled to a socket (8) to be mounted on a thigh part (7), an oil chamber (13) formed in the cylinder tube, and an oil (19) filled in the oil chamber (13), and a rod (14) coupled to an artificial lower leg part (9), and a piston (15) that divides the oil chamber (13) into a first oil chamber (13a) and a second oil chamber (13b) and that moves with the movement of the rod (14), the knee joint component (4) comprising; a first passage (20) connecting the first oil chamber (13a) and the second oil chamber (13b), and having a first passage characteristic as the oil (19) passes through when the piston (15) is moving from the first oil chamber (13a) toward the second oil chamber (13b); a second passage (30) arranged so as to be parallel to the first passage (20), and having a second passage characteristic in which a hydraulic resistance of the oil (19) is higher than that of the first characteristic when the piston (15) is moving from the first oil chamber (13a) toward the second oil chamber (13b); a third oil passage (50) connecting the first oil chamber (13a) and the second oil chamber (13b), and is passed through the oil (19) when the piston (15) is moving from the second oil chamber (13b) toward the first oil chamber (13a); a switching mechanism (50) for switching whether the oil (19) passes through either the first oil passage (20) or the second oil passage (30); and the second oil passage (30) has an inlet/outlet (31,32) of the oil (19) on the way; and the switching mechanism (50) has a first rotating member (52) that rotatably attached around a first rotating shaft (53), and that rotating around the first rotating shaft (53) when the artificial lower leg part (9) is tilted, and that switching the oil (19) through either the first oil passage (20) or the second oil passage (30) by opening or closing the inlet/outlet (31,32) of the second oil passage (30).

According to the knee joint component (4), the knee joint of the artificial leg (1) can be moved close to the movement of the knee of the human body with a simple configuration. That is, the knee joint component (4) is mounted on the hydraulic cylinder (10) mounted between the socket (8) of the thigh part (7) and the artificial lower leg part (9) in the artificial leg (1), and includes the switching mechanism (50) that switches whether the oil (19) is allowed to flow into the first oil passage (20) connecting the first oil chamber (13a) and the second oil chamber (13b) in the hydraulic cylinder or the second oil passages (30) arranged in parallel with the first oil passage (20). The switching mechanism (50) rotates around the first rotating shaft (53) when the artificial lower leg part (9) is inclined, and switches whether the oil (19) passes through the first oil passage (20) or the second oil passage (30) by opening or closing the inlet/outlet (31, 32) of the oil (19) provided in the middle of the second oil passage (30).

As described above, the path of the oil (19) can be switched between the first oil passage (20) and the second oil passage (30) by the switching mechanism (50) having a simple structure of switching the path of the oil (19) when the artificial lower leg part (9) is tilted by rotating around the first rotating shaft (53). The passage characteristics of the oil (19) in the first oil passage (20) and the second oil passage (30) are different. Therefore, the knee joint movement can be made different between the case where the knee joint (2) is extended (the artificial lower leg part (9) is not tilted) and the case where the knee joint (2) is refracted (the artificial lower leg part (9) is tilted) in the walking state by attaching the artificial leg (1) to the thigh part (7), and the knee joint can be made close to the movement of the knee of the human body.

Application Example 2

In the knee joint component (4) according to the application example 1, the switching mechanism (50) is rotatably mounted around a second rotating shaft (56) of the first rotating member (52), when the artificial lower leg part (9) is inclined, the second rotating shaft (56) is rotated around, instead of the first rotating member (52), the inlet/outlet (31,32) of the second oil passage (30) in an open state or a closed state, the oil (19) is provided with a second rotating member (55) for switching whether to pass through the first oil passage (20) or the second oil passage (30).

As described above, the second rotating member (55) rotatably mounted around the second rotating shaft (56) of the first rotating member (52) rotating around the first rotating shaft 53 switches whether the oil (19) passes through the first oil passage (20) or the second oil passage (30) by opening or closing the inlet/outlet (31, 32) of the second oil passage (30) instead of the first rotating member (52), In other words, by performing the switching of the first oil passage (20) and the second oil passage (30) in a form such as a so-called double pendulum, it is possible to provide a switching mechanism (50) which reacts with the slope of the artificial lower leg part (9) more sensitively.

Application Example 3

A knee joint component (6) in the knee joint component (4, 5) according to Application Example 1 or Application Example 2, the third oil passage (40) has a third passage characteristic in which a hydraulic resistance of the oil (19) is lower than that of the first characteristic and the second characteristic, and are provided with a plurality of inlet/outlet (75,76) of the oil (19) from the first oil chamber (13a) to a second oil chamber (13b) in the direction of movement of the piston (15) in the first oil chamber (13a).

In such a knee joint component (6), the third oil passage (40) is provided with a third passage characteristic having a hydraulic resistance lower than the first passage characteristic and the second passage characteristic, and a plurality of inlet/outlet (75, 76) of the oil (19) from the second oil chamber (13b) to the first oil chamber (13a) are provided in the moving direction of the piston (15) in the second oil chamber (13b). As a result, when the piston (15) moves in the contracting direction, the oil (19) flows from the second oil chamber (13b) into the first oil chamber (13a) via the first oil passage (20) and the second oil passage (30). When the piston (15) moves in the extending direction, the oil (19) flows from the first oil chamber (13a) into the second oil chamber (13b) via the third oil passage (40). At this time, since the passage characteristics of the first oil passage (20), the second oil passage (30) and the third oil passage (40) are different, the movement of the artificial leg (1) can be made closer to the actual movement of the leg.

Application Example 4

A knee joint (2) according to the present invention comprises: a cylinder tube (12) coupled to a socket (8); an oil chamber (13) formed inside the cylinder tube (12); an oil (19) filled in the oil chamber (13); a rod (14) coupled to the artificial lower leg part (9); a hydraulic cylinder (10) arranged in the oil chamber (13) and partitioning the oil chamber (13) into a first oil chamber (13a) and a second oil chamber (13b) and moving with the movement of the rod (14); and knee joint components (4, 5, 6) according to any one of Applications 1 to 3. Such the knee joint (2) may be a knee joint (2) having the characteristics of the knee joint component (4, 5, 6) according to any one of Applications 1 to 3.

Application Example 5

An artificial leg (1) according to the present invention has a socket (8) mounted on the thigh part (7), an artificial lower leg part (9), and a knee joint (2) described in Application Example 4. Such an artificial leg (1) may be an artificial leg (1) having the features of the knee joint (2) described in Application Example 4.

BRIEF DESCRIPTION OF DRAWINGS

FIGS. 10(A) to 10(D) are diagrams showing the operation of the knee joint during a heel contact period to a foot flat period of a stance phase in the third embodiment.

FIGS. 11 (A) to (D) are diagrams showing the operation of the knee joint during a heel-off period of the stance phase, a crossing period of the stance phase, to an acceleration period of the swing phase in the third embodiment.

FIGS. 12(A) to 12(D) are diagrams showing the operation of the knee joint during a mid-swing period to a deceleration period of the swing phase in the third embodiment.

FIGS. 13 (A) to-(D) are diagrams showing the operation of the knee joint during the deceleration period to heel contact period in the third embodiment.

FIG. 14(A) to (F) are diagrams showing a schematic appearance view of a knee joint in the fourth embodiment, a relationship between the position of the lever and the bending resistance when the mode switching of the oil passage of the knee joint component is performed, and a case where the state is a locked state.

DESCRIPTION OF EMBODIMENTS

Hereinafter, embodiments to which the present invention is applied will be described with reference to the accompanying drawings. It should be noted that the embodiments of the present invention are not limited to the following embodiments in any way, and various forms may be taken as long as they belong to the technical scope of the present invention.

First Embodiment

The first embodiment will be described with reference to FIGS. 1 to 5.

<Composition of Artificial Leg>

Figure 1:
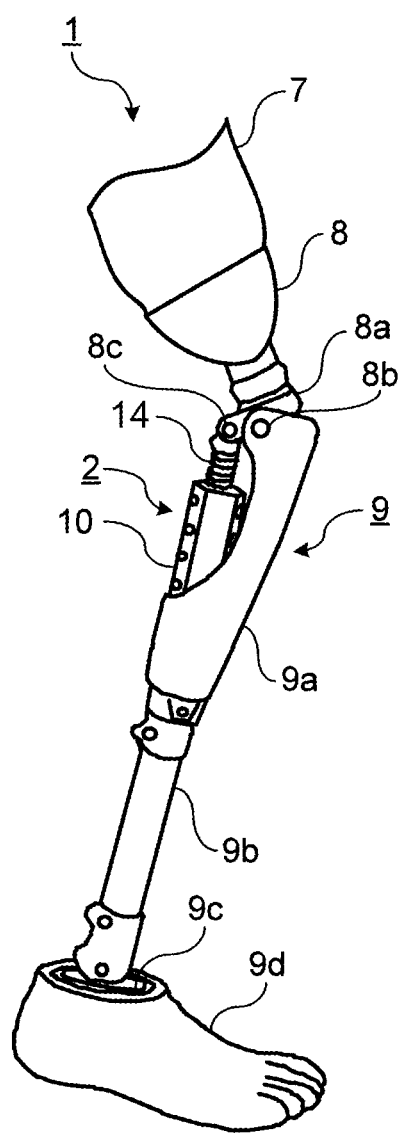
FIG. 1 is a diagram illustrating a schematic configuration of an artificial leg.

First, the overall configuration of an artificial leg 1 will be described with reference to FIG. 1. FIG. 1 is a diagram illustrating a schematic configuration of an artificial leg 1 to which the present invention is applied;

As shown in FIG. 1, the artificial leg 1 comprises a socket 8, an artificial lower leg part 9, and a knee joint 2. The socket 8 is a portion for attaching the artificial leg 1 to a thigh part 7 of a user, and is adapted so as not to impose a burden on the thigh part 7 of the user by forming a resilient material such as resin so as to fit the shape of the thigh part 7 of the user.

The lower end of the socket 8 is provided with a connecting portion 8a for connecting the socket to the artificial lower leg part 9 and the knee joint 2. The lower end of the connection portion 8a is a linkage mechanism, and is connected to the upper end portion of the artificial lower leg part 9 by a bolt 8b at a portion close to the center portion of the socket 8, and the artificial lower leg part 9 is bent with respect to the socket 8 about the bolt 8b.

Further, the distal end of a rod 14 of the knee joint 2 to the distal end portion of the lower end of the connecting portion 8a is connected by a bolt 8c. By connecting the connecting portion 8a to the rod 14 of the socket 8 in this way, when the rod 14 is expanded and contracted, the socket 8 (thigh part 7) and the artificial lower leg part 9 is refractive operation. The hydraulic cylinder 10 of the knee joint 2 and a knee joint component 4 (which will be described later in detail) are integrated and fixed to the artificial lower leg part 9 in a state of being enclosed in the artificial lower leg part 9 by a bolt (not shown) or the like.

As shown in FIG. 1, the artificial lower leg part 9 is formed in a shape simulating the lower leg of a human leg. The upper part (hereinafter referred to as a upper lower leg 9a) is connected to the sockets 8 and includes the hydraulic cylinder 10 and the knee joint component 4, and is formed using a light metal such as aluminum or a highly strong resin such as CFRP.

In addition, among the artificial lower leg part 9, a portion (hereinafter, referred to as a shin part 9b) which hits a so-called shin below the upper lower leg 9a is formed using a light metal such as aluminum or a highly strong resin such as CFRP. Further, a portion of the lower portion of the shin part 9b, corresponding to the foot, is composed of a connected portion 9c of a metallic portion coupled to the shin part 9b and a foot 9d coated with a resin such as urethane.

<Composition of Knee Joint>

Figure 2:
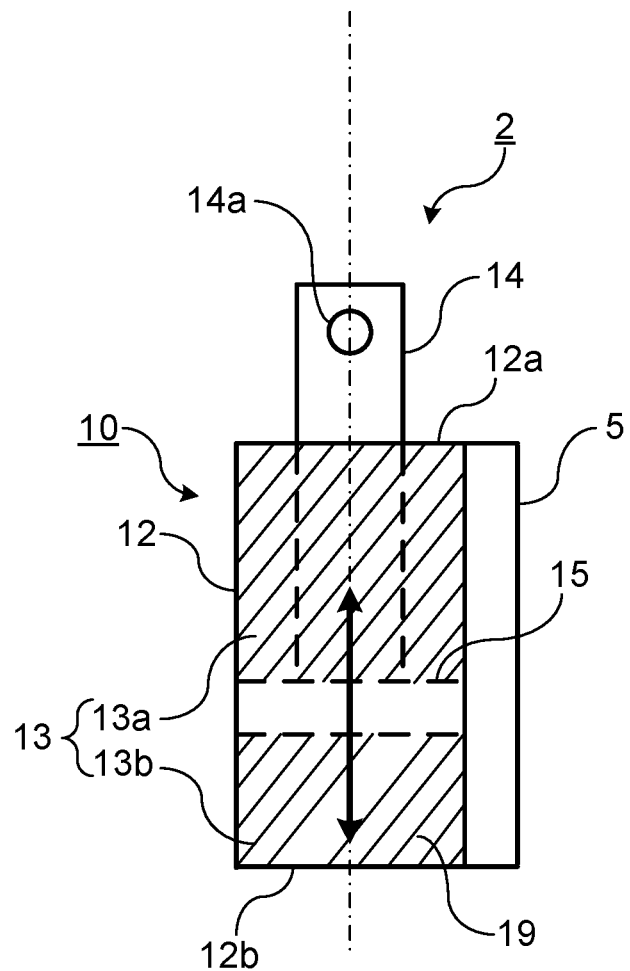
FIG. 2 is a diagram showing a schematic configuration of a knee joint.

Next, the configuration of the knee joint 2 will be described with reference to FIG. 2. FIG. 2 is a diagram showing a schematic configuration of the knee joint 2.

As shown in FIG. 2, the knee joint 2 comprises a hydraulic cylinder 10 and a knee joint component 4. The hydraulic cylinder 10 comprises a cylinder tube 12, an oil chamber 13, a rod 14, and a piston 15. The oil chamber 13 is filled with oil 19(hydraulic oil).

A cylinder tube 12 is a hydraulic cylinder in which a metal such as aluminum is formed in a cylindrical shape, and both end surface of the cylinder tube s 12a, 12b are closed by the same material as the cylindrical portion. Further, the end surface 12a has a hole for inserting the rod 14. The outer shape of the cylinder tube 12 has a substantially rectangular parallelepiped, the knee joint component 4 on one side thereof is fixed by a bolt (not shown) (knee joint component 4 will be described in detail later).

Oil chamber 13 is a space formed inside the cylinder tube 12, the oil 19 is filled as a hydraulic oil. A piston 15 is disposed in the oil chamber 13, and the oil chamber 13 is divided by a first oil chamber 13a and a second oil chamber 13b.

A rod 14 made of a metal such as aluminum in a rod shape is attached to the piston 15 (the piston 15 and the rod 14 may be integrally molded). Further, the end portion of the rod 14 is provided a hole portion 14a for coupling with the connecting portion 8a of the socket 8, the connecting portion 8a and a hole portion 14a are connected by a, bolted 8c. Then, the piston 15 moves with the movement of the rod 14 (expansion and contraction with bending of the knee). the piston 15 is sliding in the axial direction of the central axis of the cylinder tube 12 (arrow direction in FIG. 2 in the vertical)).

<Composition of Knee Joint Components>

Figures 3, 3A, 3B:
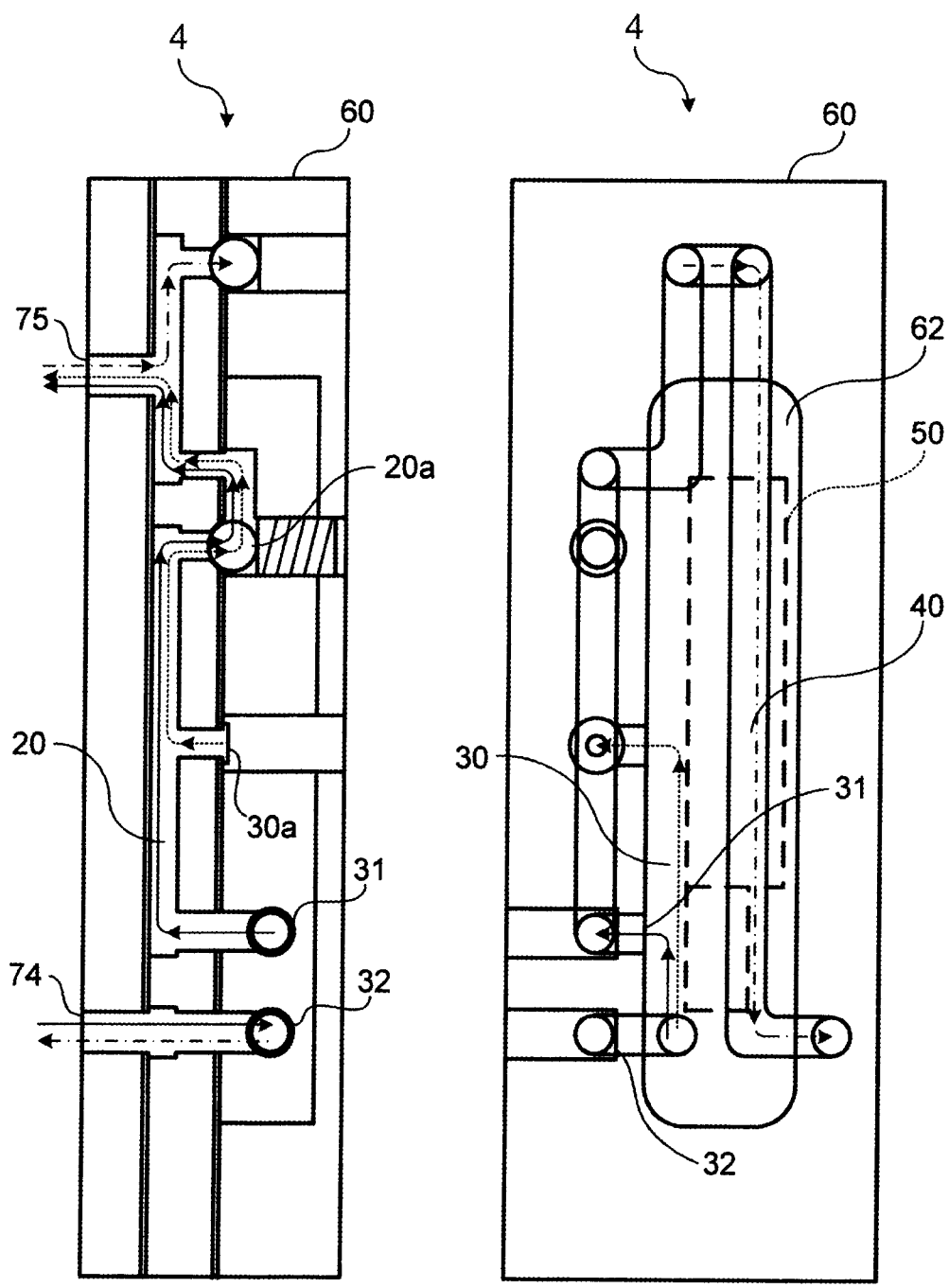
FIG. 3(A) is a side view showing a schematic configuration of the knee joint component.
FIG. 3(B) is a front view showing a schematic configuration of the knee joint component.

Next, the configuration of the knee joint component 4 will be described with reference to FIGS. 3A and 3B. FIGS. 3A and 3B are diagrams showing a schematic configuration of the knee joint component 4, FIG. 3A is a side view of the knee joint component 4, and FIG. 3B is a front view.

As shown in FIGS. 3A and 3B, the knee joint component 4 includes a body 60, a first oil passage 20 and a second oil passage 30 provided inside the body 60, and a switching mechanism 50. Body 60 is a component attached to the side surface of the hydraulic cylinder 10, is a substantially rectangular parallelepiped-shaped block made of resin. The hydraulic cylinder 10 is coupled by a plurality of bolts (not shown). the first oil passage 20, the second oil passage 30, a third oil passage 40, an oil chamber 62, and inlets/outlets 74, 75 are formed inside the body 60, The switching mechanism 50 is provided inside the oil chamber 62. The body 60 and the hydraulic cylinder 10 are coupled so that the hydraulic circuit is formed by connecting the inlet/outlet 74,75 of the body 60 to the oil chambers 13a,13b of the hydraulic cylinder.

The first oil passage 20 is an oil passage connecting the first oil chamber 13a and the second oil chamber 13b of the cylinder tube 12, and is indicated by a solid arrow in FIGS. 3A and 3B. An orifice 20a is provided in the middle of the first oil passage 20. The orifice 20a, by providing a hole portion capable of mounting the bolt 20b to a part of the first oil passage 20, by adjusting the insertion depth with respect to the hole portion of the bolt 20b, so that the size of the passing area of the oil 19 can be adjusted.

The second oil passage 30 that is branched from the first oil passage 20 so as to be parallel with the first oil passage 20, is an oil passage for having a characteristic that the passage characteristics of the oil 19 are different from the first oil passage 20. The second oil passage 30 branched from the first oil passage 20 is indicated by a broken line arrow in FIGS. 3A and 3B. An orifice 30a is provided in the middle of the second oil passage 30.

The passage characteristics of the oil 19 in the first oil passage 20 and the second oil passage are realized by the difference in the passage areas of the oil 19 in the orifice 20a and the orifice 30a of the respective oil passages. In the present embodiment, since the direction of the oil 19 passing through area of the orifice 30a is smaller than the passing area of the oil 19 of the orifice 20a, the oil 19 is hardly passed through the second oil passage 30 than the first oil passage 20 (the hydraulic resistance of the second oil passage 30 (the second passing characteristic) is higher than the hydraulic resistance of the first oil passage 20 (the first passing characteristic)).

The third oil passage 40 is an oil passage that directly connects the first oil chamber 13a and the second oil chamber 13b. The third oil passage 40 is provided with a check valve 70 for blocking the flow of the oil 19 from the second oil chamber 13b to the first oil chamber 13a.

Further, a part of the oil chamber 62 (lower left of the oil chamber 62 in FIGS. 3A and 3B), is provided in inlet/outlets 31, 32 of the oil 19, and is part of the first oil passage 20 and the second oil passage 30. The switching mechanism 50 is a mechanism for switching whether the oil 19 passes through the first oil passage 20 or the second oil passage 30.

<Configuration of Switching Mechanism>

Figures 4, 4A, 4B:
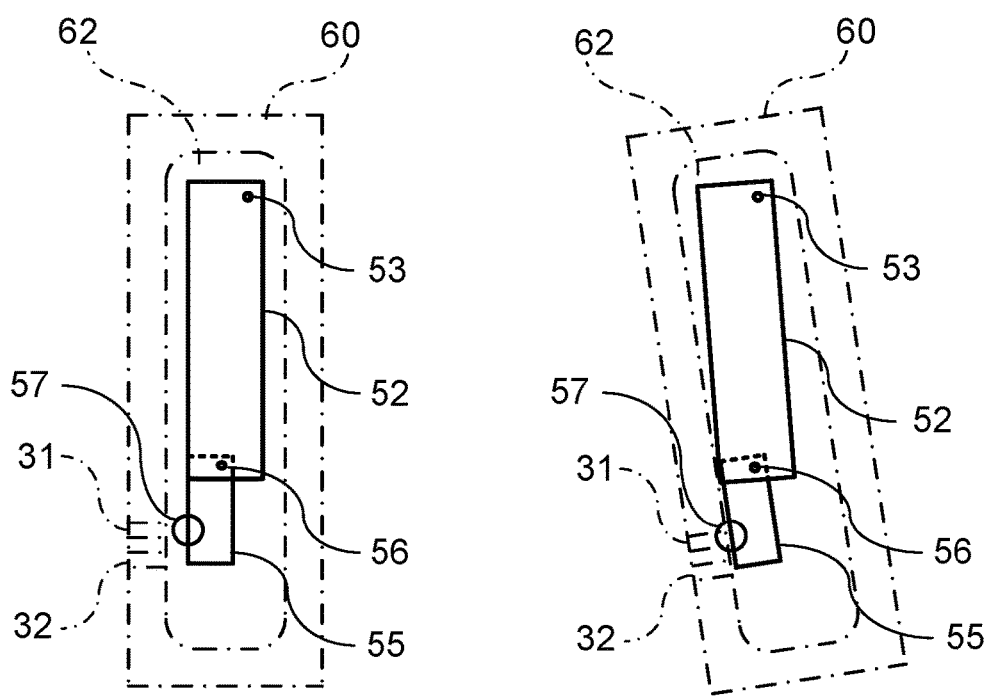
FIG. 4(A) is a diagram showing a schematic configuration of a switching mechanism.
FIG. 4(B) is a diagram showing a schematic configuration of the switching mechanism in a state in which the artificial leg is upright, and is a diagram showing a state of the switching mechanism in a state in which the artificial leg is inclined.

Next, the configuration of the switching mechanism 50 will be described with reference to FIGS. 4A and 4B. FIGS. 4A and 4B are diagrams showing a schematic configuration of the switching mechanism 50. FIG. 4A is a diagram showing a state of the switching mechanism 50 in a state in which the artificial leg 1 is upright, and FIG. 4B is a diagram showing a state of the switching mechanism 50 in a state in which the artificial leg 1 is inclined.

As shown in FIGS. 4A and 4B, the switching mechanism 50 includes a first rotating member 52 and a second rotating member 55. The first rotating member 52 is a cubic member made of metal such as brass, the first rotating shaft 53 is provided near one end in the longitudinal direction (the end portion of the vertical upper side), so as to be rotatable around the first rotating shaft 53, it is attached to the body 60 with a metal pin such as brass. Further, the second rotating shaft 56 is provided in the vicinity of the other end side of the first rotating member 52 (the end portion opposite to the end portion where the first rotating shaft 53 is provided), the second rotating member 55 to the second rotating shaft 56 rotatably, it is attached by a metal pin such as brass.

The second rotating member 55 is a cubic member made of metal such as aluminum lighter than the first rotating member 52, is attached to the second rotating shaft 56 at one end in the longitudinal direction by a pin. Further, the one end side surface of the second rotating member 55 (left side in FIG. 4 (A)), the portion facing the inlet/outlet 31 of the second oil passage 30, the metal ball 57 is press-fitted so as to form a convex portion. Then, the tip of the press-fitted metal ball 57 (convex portion) is adapted to close the inlet/outlet 31 when in close contact with the inlet/outlet 31.

Thus, the switching mechanism 50, the first rotating member 52 is rotatably attached to the body 60, the second rotating member 55 is rotatably attached to the distal end of the first rotating member 52, so-called double pendulum It has become like. Therefore, the artificial leg 1 is actuated, when the knee joint 2, i.e. the body 60 is inclined with respect to the vertical direction, the first rotating member 52 and the second rotating member 55 is rotated around the first rotating shaft 53 and the second rotating shaft 56 by its own weight. Then, the metal ball 57 attached to the side surface of the second rotating member 55 closes the inlet/outlet 31 of the second oil passage 30, and the flow passage of the oil 19 can be switched as described later. Further, since the side of the second rotating member 55 is lighter than the first rotating member 52, as compared with the case where one of the rotating member is rotated, so that more sensitive swing the tip of the second rotating member 55.

<Actuation of Knee Joint>

Figure 5:
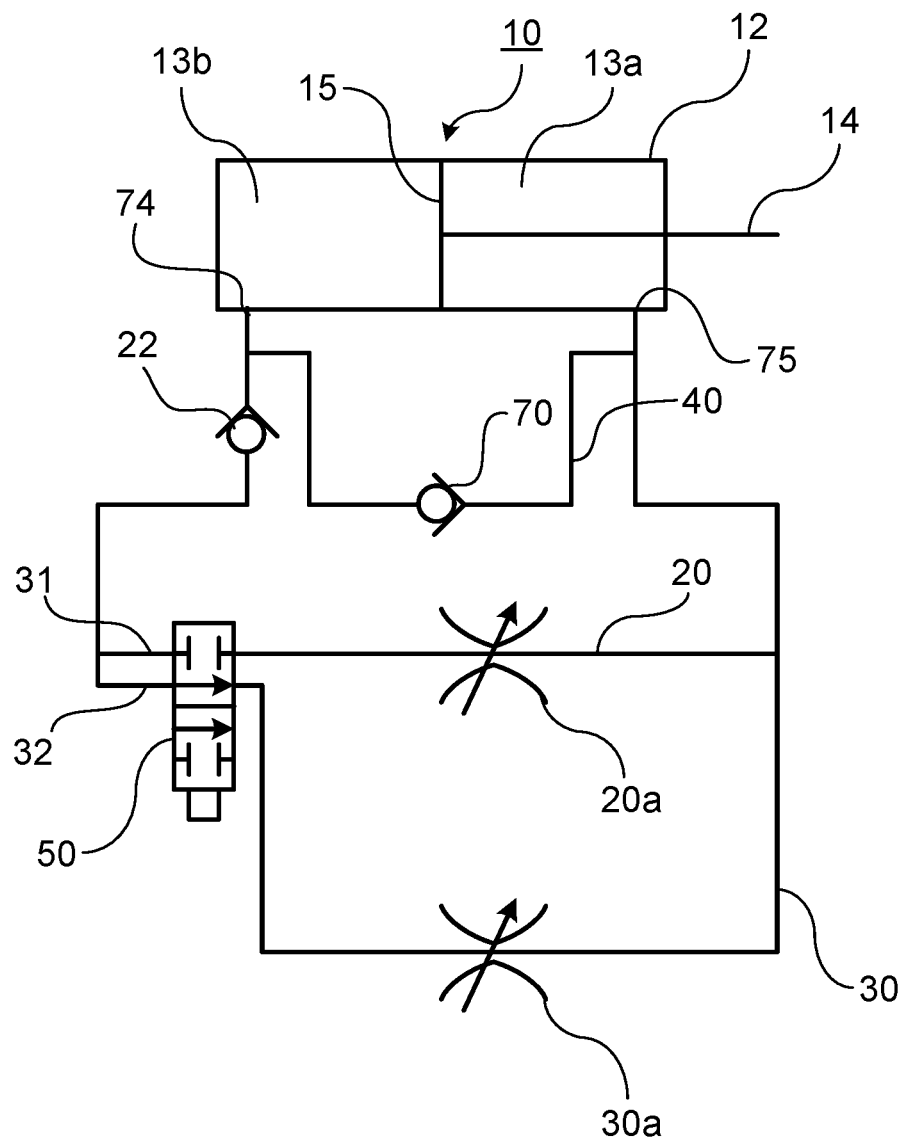
FIG. 5 is a hydraulic circuit diagram of the knee joint including the knee joint component.

Next, the operation of the knee joint 2 to which the knee joint component 4 is attached will be described with reference to FIGS. 3 (A), (B) and 5. FIG. 5 is a hydraulic circuit diagram of the knee joint 2 including the knee joint component 4.

When the knee joint 2 is in the extended state (when the artificial lower leg part 9 is not inclined or is not inclined), the switching mechanism 50 is in the vertical state or close to the vertical state, so that both of the inlet/outlet 31,32 are in the open state by the switching mechanism 50. In this case, since the passing area of the oil 19 toward the orifice 30a is low, the hydraulic resistance of the second oil passage 30 is higher than the hydraulic resistance of the first oil passage 20. Therefore, the oil 19 passes through the first oil passage 20 as shown by the solid lines in FIGS. 3 (A), (B), and FIG. 5. Then, the piston 15 of the hydraulic cylinder 10 will move faster.

When the deflection of the knee joint 2 increases (i.e., when the inclination of the artificial lower leg part 9 increases) the inlet/outlet 31 is closed and the inlet/outlet 32 is opened by the switching mechanism 50. Then, the oil 19 will pass through the second oil passage 30 as shown by broken lines in FIGS. 3 (A), (B), and FIG. 5. In this case, as described above, since the hydraulic resistance of the second oil passage 30 is higher than the hydraulic resistance of the first oil passage 20, the movement of the piston 15 of the hydraulic cylinder 10 is slowed down.

Furthermore, when the knee joint 2 extends from a state in which it is refracted, the check valve 22 is closed and the check valve 70 is opened, so the oil 19 does not flow into the first oil passage 20 and the second oil passage 30, as shown by a chain line in FIG. 3 (A), (B) and FIG. 5, the oil 19 is to flow from the oil chamber 13b to the oil chamber 13a. In The third oil passage 40 in this case, because it directly connects the first oil passage 13a and the second oil passage 13b, the hydraulic resistance is lower than the first oil passage 20 and the second oil passage 30, therefore, the piston 15 of the hydraulic cylinder 10 will move faster.

As described above, when the knee portion of the artificial leg 1 is refracted from the extended state by the knee joint 2, the knee portion is gradually hardly refracted. and when the knee is extended from the refracted state, the knee portion smoothly extends.

<Features of Artificial Leg>

In the artificial leg 1 as described above, the knee joint of the artificial leg 1 can be moved close to the movement of the knee of the human body with a simple configuration. That is, the knee joint component 4 is mounted on the hydraulic cylinder 10 mounted between the socket 8 of the thigh part 7 and the artificial lower leg part 9 in the artificial leg 1, and the oil passage is switched by the switching mechanism 50. In the switching mechanism 50, when the artificial lower leg part 9 is inclined, the first rotating member 52 is rotated around the first rotating shaft 53 by its own weight, and the second rotating member 55 is rotated around the second rotating shaft 56, whereby the inlet/outlet 31 of the oil 19, which is provided in the middle of the second oil passage 30, is opened or closed.

As a result, whether the oil 19 passes through the first oil passage 20 or the second oil passage 30 is switched. As described above, the path of the oil 19 can be switched between the first oil passage 20 and the second oil passage 30 by the switching mechanism 50 having a simple structure in which the first rotating member 52 and the second rotating member 55 rotate around the first rotating shaft 53 and the second rotating shaft 56, the first rotating member 52 and the second rotating member 55 operate like a double pendulum, and when the artificial lower leg part 9 tilts, the path of the oil 19 is switched by its own weight.

The passage characteristics of the oil 19 in the first oil passage 20 and the second oil passage 30 are different. Therefore, the knee joint movement can be made different between the case where the knee joint 2 is extended (the artificial lower leg part 9 is not inclined) and the case where the knee joint 2 is refracted (the artificial lower leg part 9 is inclined) in the walking state by mounting the artificial leg 1 on the thigh part 7, and the knee joint can be made close to the movement of the knee of the human body.

Further, by the second rotating member 55 rotatably mounted around the second rotating shaft 56 of the first rotating member 52 rotating around the first rotating shaft 53, instead of the first rotating member 52, the inlet/outlet 31, 32 of the second oil passage 30 are opened or closed to switch whether the oil 19 passes through the first oil passage 20 or the second oil passage 30. In other words, by performing the switching of the first oil passage 20 and the second oil passage 30 in a form such as a so-called double pendulum, it is possible to provide a switching mechanism 50 which reacts with the slope of the artificial lower leg part 9 more sensitively.

Second Embodiment

Next, the second embodiment will be described with reference to FIGS. 6A and 6B. In the second embodiment, since the structures of the artificial leg 1 and the knee joint 2 are the same as those in the first embodiment, the description thereof will be omitted, and the knee joint component 5 different from the first embodiment will be described.

Figures 6, 6A, 6B:
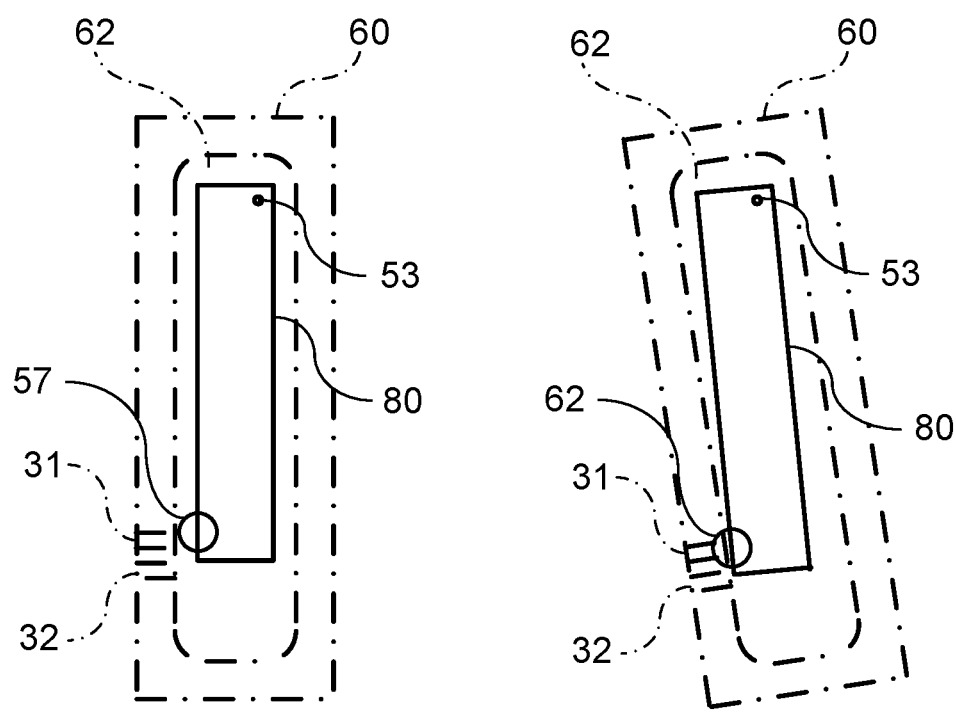
FIG. 6(A) is a diagram showing a schematic configuration of a switching mechanism in the second embodiment, showing a state of a switching mechanism in a state in which a artificial leg is upright.
FIG. 6(B) is a diagram showing a schematic configuration of the switching mechanism in the second embodiment, showing a state of the switching mechanism in a state in which the artificial leg is inclined.

As shown in FIGS. 6A and 6B, in the knee joint component 5 according to the second embodiment, the rotating member of the switching mechanism 50 is only one of the third rotating member 80. The third rotating member 80 is rotatably mounted around the first rotating shaft 53, when the artificial lower leg part 9 is inclined, by its own weight, rotates around the first rotating shaft 53, the inlet/outlet 31,32 of the second oil passage 30 in the same manner as in the first embodiment to the open or closed state. Thereby, it is possible to switch whether the oil 19 passes through the first oil passage 20 or the second oil passage 30.

In the switching mechanism 50 in the second embodiment, since the rotating member is only one (third rotating member 80), as compared with the case of using the two rotating members in the first embodiment (the first rotating member 52, the second rotating member 55), although the operating sensitivity is inferior, it is possible to very simplify the structure, it is possible to reduce the weight and cost.

Third Embodiment

Figures 7, 7A, 7B, 7C:
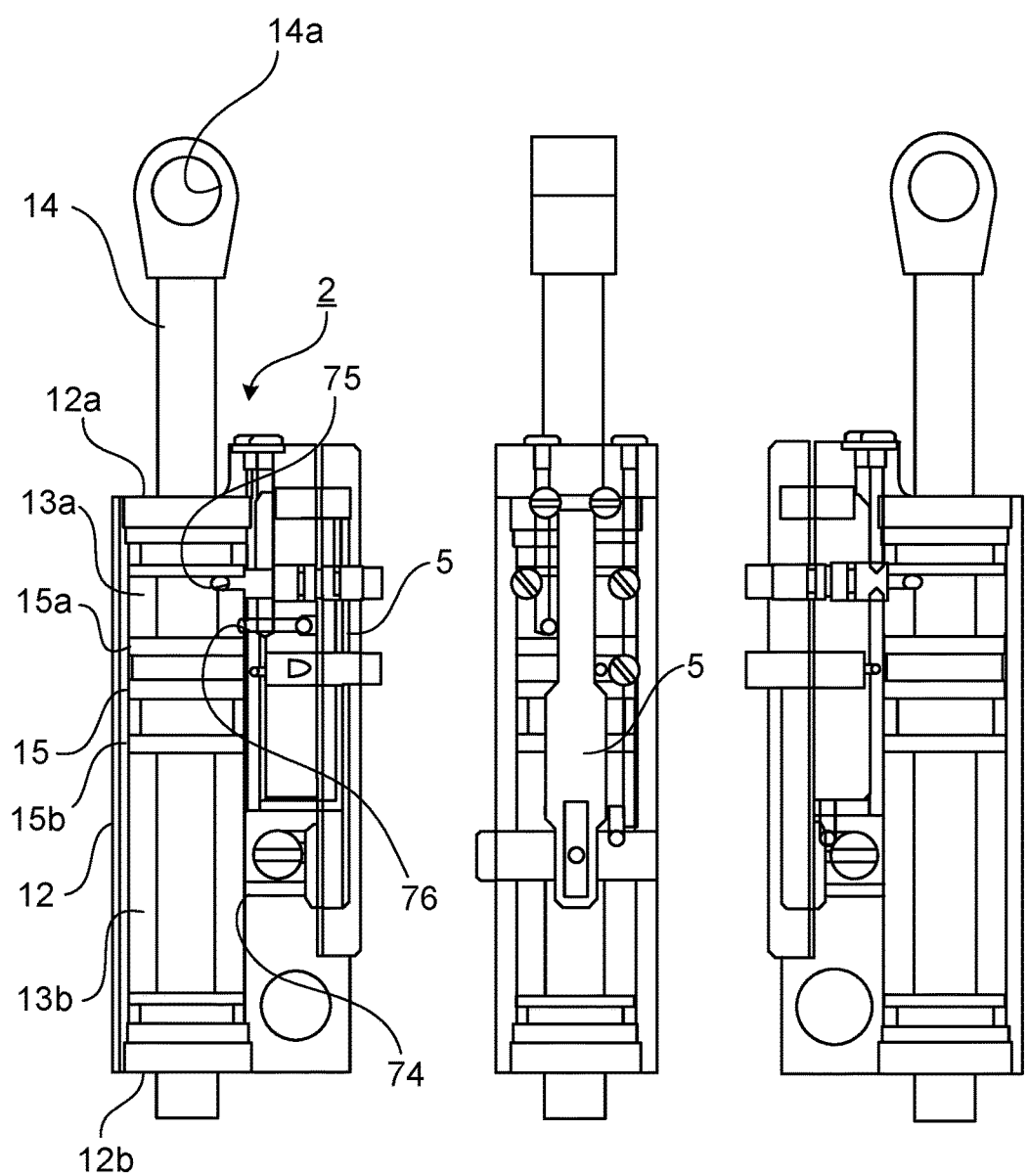
FIGS. 7(A) to 7(C) are diagrams showing a configuration of a knee joint to which a knee joint component according to the third embodiment is applied.
Figure 8:
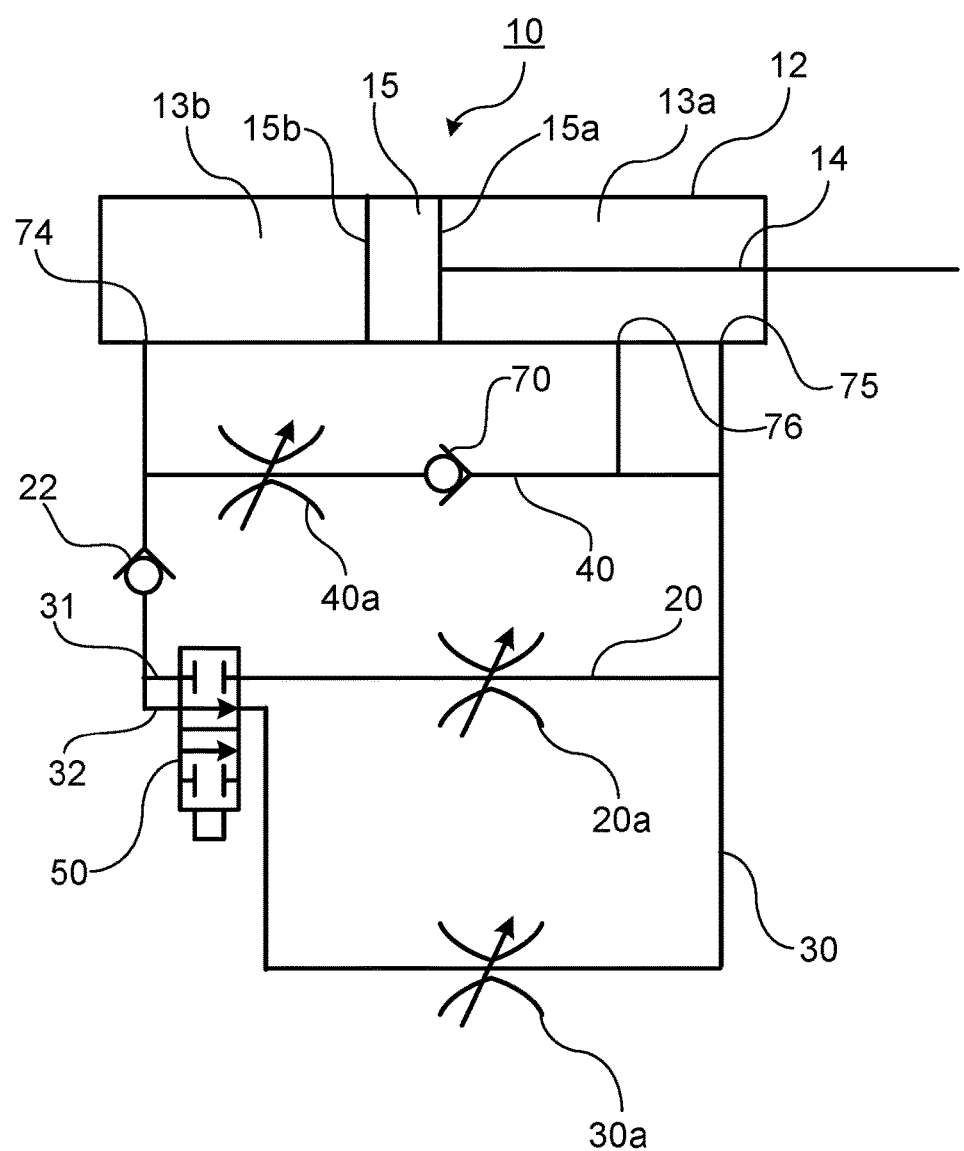
FIG. 8 is a hydraulic circuit diagram of the knee joint to which the knee joint component according to the third embodiment is applied.

Next, a third embodiment will be described with reference to FIGS. 7 to 13. FIGS. 7 (A) to (C) are diagrams showing the configuration of the knee joint 2 to which the knee joint component 6 is applied, and FIG. 8 is a hydraulic circuit diagram of the knee joint 2 to which the knee joint component 6 is applied. Also in the third embodiment, since the structure of the artificial leg 1 is the same as that in the first embodiment, the description thereof is omitted, and the knee joint 2 and the knee joint component 6 different from those in the first embodiment will be described.

<Composition of Knee Joints and Knee Joint Components>

As shown in FIGS. 7 (A) to (C), in the knee joint 2 in the third embodiment, the ring portion of the piston 15 is doubled (one of the ring portions is referred to as a ring 15a and the other is referred to as a ring 15b). A space may or may not exist between the rings 15a and 15b. In addition, unlike the first and second embodiments, the rod 14 extends on both end sides of the piston 15 (in the vertical direction in FIGS. 7A to 7C). Furthermore, the rod 14 is adapted to penetrate not only the end surface 12a of the cylinder tube 12 but also the end surface 12b.

In the knee joint component 6 according to the third embodiment, as shown in the hydraulic circuit diagram of FIG. 8, the third oil passage 40 connects the first oil chamber 13a and the second oil chamber 13b via the inlet/outlet 74 and the inlet/outlet 75, and connects the first oil chamber 13a and the second oil chamber 13b via the inlet/outlet 74 and the inlet/outlet 76. In other words, the oil passage connected to the inlet/outlet 74 is branched and connected to the inlet/outlet 75 and the inlet/outlet 76.

Further, in the third oil passage 40, the orifice 40a is provided at the inlet/outlet 74 side than the branch point where the oil passage is divided into the inlet/outlet 75 and the inlet/outlet 76. The orifice 40a, the third oil passage 40 is set to have a third passing characteristic hydraulic resistance is lower than the first passing characteristic and the second passing characteristic. In the third oil passage 40 according to the third embodiment, in the first oil chamber 13a, two inlet/outlet 75, 76 of the oil 19 from the first oil chamber 13a to the second oil chamber 13b are provided at different positions in the moving direction of the piston 15.

<Actuation of Knee Joint>

Figure 9:
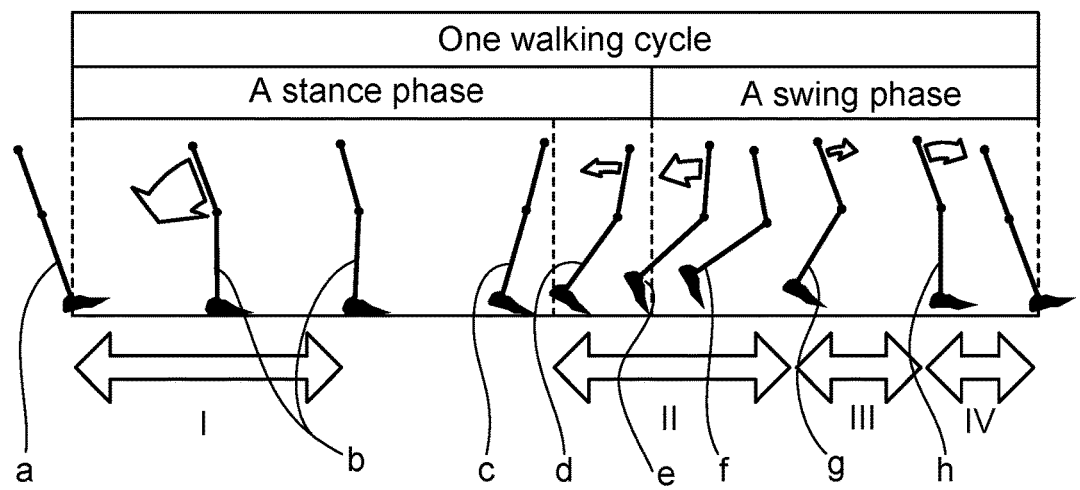
FIG. 9 is a view showing the movement of the artificial leg in the third embodiment when a user wearing the artificial leg performs walking.

Next, the operation of the knee joint 2 will be described with reference to FIGS. 9 to 13. FIG. 9 is a view showing the movement of the artificial leg 1 when the user wearing the artificial leg 1 performs walking. FIGS. 10 to 13 are diagrams showing the operation of the knee joint fitting 6 in the stance phase and the swing phase during walking.

As shown in FIG. 9, when a person who is a user of the artificial leg 1 walks, one walking cycle, in which the heel of one foot touches the ground and then the heel touches the ground, is composed of movements called a stance phase and a swing phase. The stance phase is a phase during which the foot is on the floor during walking and weight is applied, and is subdivided into five phases: a heel contact period (shown in (a) of FIG. 9), a foot flat period (shown in (b) of FIG. 9), a mid-stance period (shown in (c) of FIG. 9), a heel contact period (shown in (d) of FIG. 9), and a step-off period (shown in (e) of FIG. 9). The Swing phase is a phase from when the toe leaves the ground to the next heel touchdown, that is, a period during which the foot is swung away from the ground during walking, and is subdivided into three period: an acceleration period (shown in FIG. 9 (*f*)), a mid-swing period (shown in FIG. 9 (*g*)), and a deceleration period (shown in FIG. 9 (*h*)).

In the stance phase, a particularly strong hydraulic resistance is generated in the knee joint 2 to suppress the knee fracture in two states (shown by (I) in FIG. 9) of the heel contact period (a) and the foot flat period (b), In addition, during a period up to the heel-off period (d) of the stance phase, the step-off period (e) of the stance phase, and the acceleration period (f) of the swing-phase (indicated by (II) in FIG. 9), an appropriate hydraulic resistance is generated in the knee joint 2 to quickly shift to the swing phase.

During the mid-swing period (g) of the swing phase to the deceleration period (h) of the swing phase (indicated by (III) in FIG. 9), a weak hydraulic resistance is generated in the knee joint 2 to quickly shift to the heel contact period (a), In addition, during the period from the deceleration period (h) to the heel contact period (a) (indicated by (IV) in FIG. 9), a strong hydraulic resistance is generated to alleviate the impact at the time of full extension (heel contact period (a)).

In order to realize the operation in the stance phase and the swing phase, the knee joint 2 operates as shown in FIGS. 10 to 13. In FIGS. 10 to 13, (A) shows the state of the flexion of the artificial leg 1 in the stance phase and the swing phase in the walking cycle, (B) shows the configuration of the knee joint 2 when viewed from the front, (C) shows the configuration when viewed from the side, and (D) shows the configuration when viewed from the back.

First, during the heel contact period (a) to the foot flat period (b) of the stance phase (indicated by (I) in FIG. 10(A)), the piston 15 moves downward from the vicinity of the uppermost portion as indicated by a thick arrow in FIG. 10(B). At this time, as shown in FIG. 10A, the knee joint component 6 is inclined to the rear side of the artificial leg 1. Therefore, as shown in FIG. 10 (B), the metal ball 57 which is attached to the side surface of the second rotating member 55 closes the inlet/outlet 31 of the second oil passage 30, due to the own weight of the first rotating member 52 and the second rotating member 55. Then, the oil 19 passes through the second oil passage 30 as indicated by the thin arrows in FIGS. 10(B) to 10(D). In this case, since the hydraulic resistance of the second oil passage 30 is higher than the hydraulic resistance of the first oil passage 20, the piston 15 of the hydraulic cylinder 10 moves slowly (descending). In this case, since the check valve 70 is provided in the third oil passage 40, the oil 19 does not flow from the second oil chamber 13*b* to the first oil chamber 13*a* via the third oil passage 40. Therefore, the piston 15 does not operate.

Next, during the heel-off period (d) of the stance phase, the step-off period (e) of the stance phase and the acceleration period (f) of the swing phase (indicated by (I) in FIG. 11A), the piston 15 moves downward as indicated by the thick arrow in FIG. 11B. At this time, since the knee joint component 6 is inclined toward the front side of the artificial leg 1 as shown in FIG. 11A, the metal ball 57 on the side surface of the second rotating member 55 opens the inlet/outlet 31 of the second oil passage 30 and closes the inlet/outlet 32 as shown in FIG. 11B. Then, as shown by the thin arrows in FIGS. 11B to 11D, the oil 19 passes through the first oil passage 20. In this case, since the hydraulic resistance of the first oil passage 20 is lower than the hydraulic resistance of the second oil passage 30, the piston 15 of the hydraulic cylinder 10 moves quickly (descending). In this case, since the check valve 70 is provided in the third oil passage 40, the oil 19 does not flow from the second oil chamber 13*b* to the first oil chamber 13*a* via the third oil passage 40. Therefore, the piston 15 does not operate.

Next, during the mid-swing period (g) to the deceleration period (h) (indicated by (III) in FIG. 12A) of the swing phase, the piston 15 moves upward as indicated by a thick arrow in FIG. 12B. At this time, since the knee joint component 6 is inclined toward the front side of the artificial leg 1 as shown in FIG. 12A, the metal ball 57 on the side surface of the second rotating member 55 opens the inlet/outlet 31 of the second oil passage 30 and closes the inlet/outlet 32 as shown in FIG. 12B. Then, as shown by the thin arrows in FIGS. 12B to 12D, the oil 19 passes through the third oil passage 40 via both the inlet/outlet 75 and the inlet/outlet 76 of the first oil chamber 13*a*. Here, since the hydraulic resistance of the third oil passage 40 is very small, the piston 15 moves quickly (rising), In this case, the oil 19 in the first oil chamber 13*a* tries to flow out to the first oil passage 20 and the second oil passage 30 via the inlet/outlet 75,76, but the check valve 22 prevents the oil 19 in the first oil passage 20 and the second oil passage 30 from flowing out. Therefore, the oil 19 flows out from the first oil chamber 13*a* to the second oil chamber 13*b* only by the third oil passage 40.

Next, during a period from the deceleration period (h) to the heel contact period (a) (indicated by (IV) in FIG. 13), the piston 15 moves upward as indicated by a thick arrow in FIG. 13B. At this time, since the knee joint component 6 is inclined toward the front side of the artificial leg 1 as shown in FIG. 13A, the metal ball 57 on the side surface of the second rotating member 55 opens the inlet/outlet 31 of the second oil passage 30 as shown in FIG. 13B. Then, as shown by the thin arrows in FIGS. 13(B) to 13(D), the oil 19 tries to pass through the second oil passage 30 only through the inlet/outlet 75. Since the second oil passage 30 is blocked by the check valve 22, the oil 19 cannot pass through both the first oil passage 20 and the second oil passage 30. That is, since the oil 19 spills from the first oil chamber 13*a* to the second oil chamber 13*b* via the third oil passage 40 only from the inlet/outlet 75, Compared to the period from the mid-swing period e (g) to the deceleration period (h) of the swing phase shown in FIG. 12 (A) in (III), because strong pressure resistance is applied, so it is possible to mitigate the impact of the full extension (a).

Thus, the hydraulic resistance of the third oil passage 40, the hydraulic resistance of the first oil passage 20 (first passage characteristic) and the hydraulic resistance of the second oil passage 30 (the third passage characteristic) with the orifice 40*a* so as to be lower than the provided in the third oil passage 40, the cylinder tube 12 by providing the two inlet and outlet 75 and the inlet and outlet 76, as shown in FIG. 9, the movement of the artificial leg 1, it is possible to be closer to the movement of the leg of the more user.

Fourth Embodiment

Figures 14, 14F:
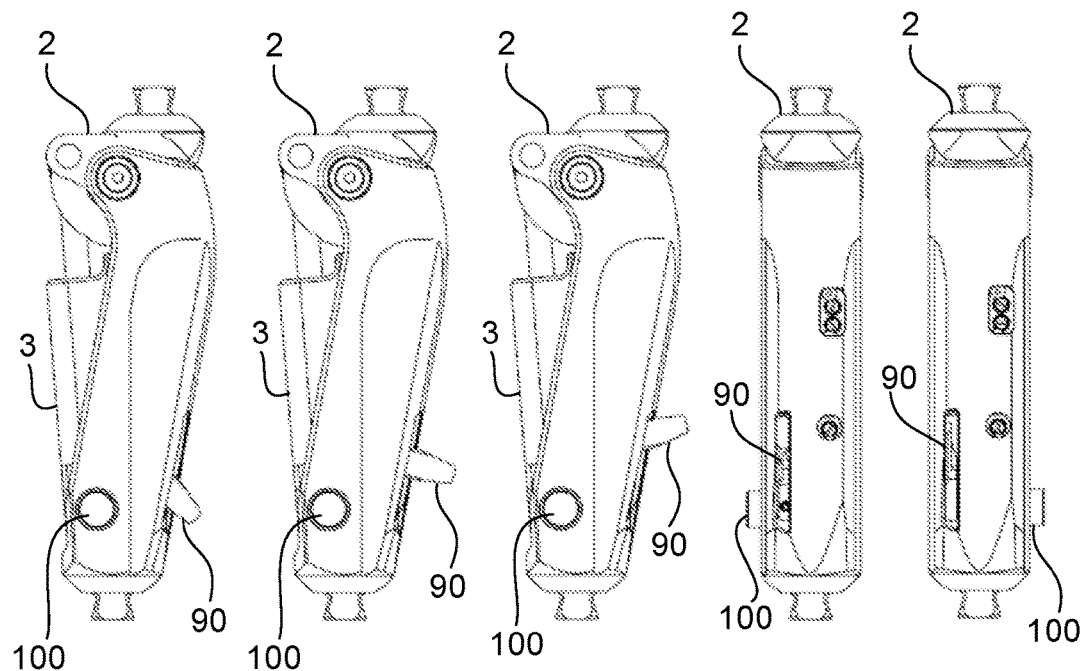

Next, a fourth embodiment will be described with reference to FIGS. 14 to 17. FIGS. 14 (A) to (F) are diagrams illustrating a schematic appearance view of the knee joint 2 in the fourth embodiment, a relationship between the position of the lever 90 and the bending resistance when the mode switching of the oil passage of the knee joint component 3 is performed, and a case where the state is a locked state. In the fourth embodiment, since the structure of the artificial leg 1 is similar to that in the first embodiment, the same components and portions having the same structure are denoted by the same reference numerals, and descriptions thereof are omitted.

The knee joint component 3 in the fourth embodiment is a knee joint component in which a lever 90 is provided on the knee joint components 4, 5, and 6 in the first embodiment to the second embodiment so as to switch the mode of the oil passage, and a stopper 100 is provided so as to fix the knee joint components 4 to 6 regardless of the use state of the artificial leg 1 (referred to as a "locked state" as shown in FIG. 14 (E)).

Here, the mode switching of the oil passage means switching of the use state of the knee joint components 3 to 6 of the first to third embodiments (referred to as "normal state"; see FIG. 14(A)) when the artificial leg 1 is used, the state in which the knee joint components 4 to 6 flex freely regardless of the use state (referred to as "free state"; see FIG. 14(B)), the state in which the flexion resistance uniformly increases when the knee joint components 4 to 6 are flexed (referred to as "yield state"; see FIG. 14(C)), or the like.

Figure 15:
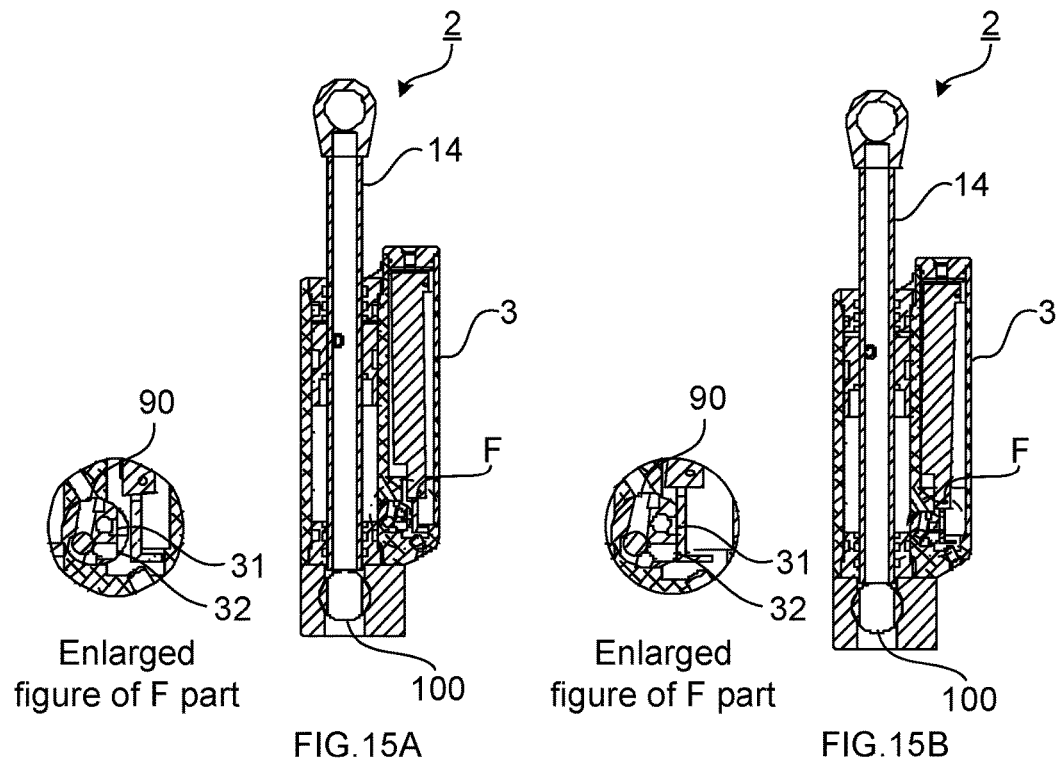
FIG. 15 (A) to (D) are diagram showing an operation of state inside the knee joint component in each mode, in the fourth embodiment.

Next, the operating state of the knee joint component 3 in each mode when the mode switching is performed will be described with reference to FIGS. 15 and 16. FIGS. 15 (A) to (D) are diagrams illustrating an operating state inside the knee joint component 3 in each mode, and FIG. 16 is a diagram schematically illustrating a state of the hydraulic circuit in each mode.

Figure 16:
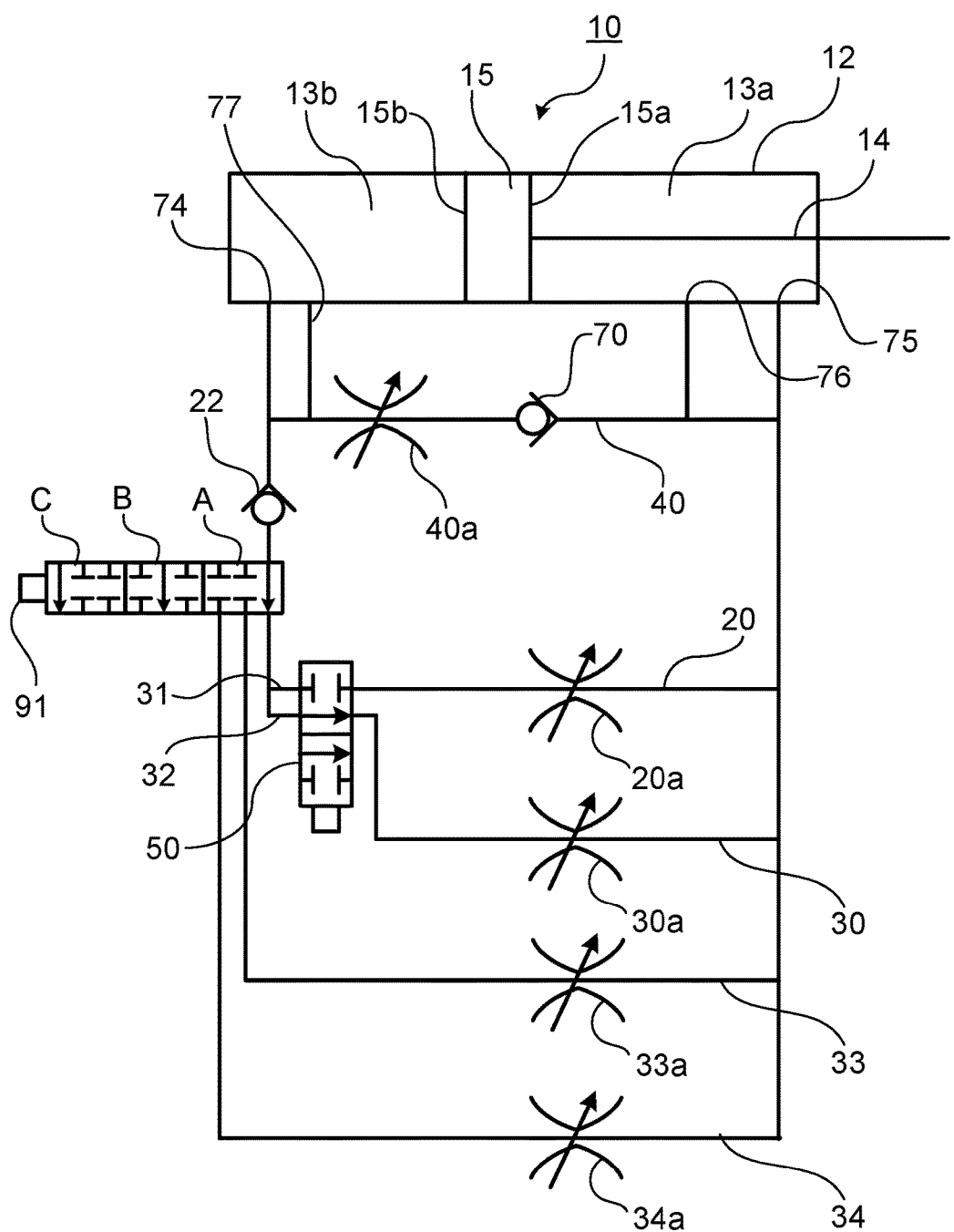
FIG. 16 is a diagram schematically showing the state of the hydraulic circuit in each mode, in the fourth embodiment.

As shown in FIG. 15 (A), the switching valve 91 for switching the oil path by rotating by the lever 90 is provided between the inlet/outlet 31, 32 and the check valve 22 of the oil passage (see FIG. 16). The switching valve 91 by rotating the lever 90 to switch the oil path, it is possible to switch the mode. The operating status of the knee joint component 3 and the status of the hydraulic circuit in each mode are shown in (V) to (VII) below.

(V) Normal State

In the normal state, in the inside of the knee joint component 3, by placing the lever 90 in the lower position, the switching valve 91, as shown in FIG. 15 (A), is a position to open the inlet/outlet 31. At this time the state of the switching valve 91 in the hydraulic circuit is as shown in "A" in FIG. 16. At this time, the oil passage passes through the inlet/outlet 31. Thus, in the normal state, the knee joint component 3 operates in the same manner as the knee joint components 4 to 6 described in the first to third embodiments. That is, as shown in FIG. 14F, in the normal state, the bending resistance is weaker when the artificial leg 1 is tilted forward than when the artificial leg 1 is tilted backward, and the refraction resistance is stronger when the artificial leg 1 is tilted backward than when the artificial leg 1 is tilted forward.

(VI) Free State

In the free state, the inside of the knee joint component 3, by placing the lever 90 in the central position, the switching valve 91 rotates counterclockwise in FIG. 15, the state shown in FIG. 15 (C) and the first bypass 33 is formed. Further, since the projections 92 are provided on the lower end portion of the switching valve 91, the metal ball 57 of the second rotating member 55 and the third rotating member 80 of the switching mechanism 50 is not to close the inlet/outlet 31 by the projection 92. The state of the switching valve 91 in the hydraulic circuit at this time is shifted to the right from the normal state, as shown in "B" in FIG. 16. Then, the oil passage is adapted to pass through the first bypass 33 from the inlet/outlet 31 and 32. Since the hydraulic resistance of the first bypass 33 is set to be smaller than the hydraulic resistance of the second bypass 34 (indicated by the orifice 33a), in the free state, the refractive resistance in the knee joint component 3 is small, so that can be easily refracted.

(VII) Yielding State

In the yielding state, the inside of the knee joint component 3, by placing the lever 90 in the upper position, the switching valve 91 is further rotated counterclockwise in FIG. 15, the state shown in FIG. 15 (D) and the second bypass 34 is formed. The state of the switching valve 91 in the hydraulic circuit at this time is shifted further to the right from the free state, as shown in "C" in FIG. 16. Then, the oil passage is adapted to pass through the second bypass 34 from the inlet/outlet 31. The second bypass 34, since the hydraulic resistance as compared with the first bypass 33 is set to be very large (indicated by the orifice 34a), in the yielding state, the knee joint component 3, the refractive resistance is very large, so as not to unexpectedly knee folding.

Figures 17, 17A, 17B:
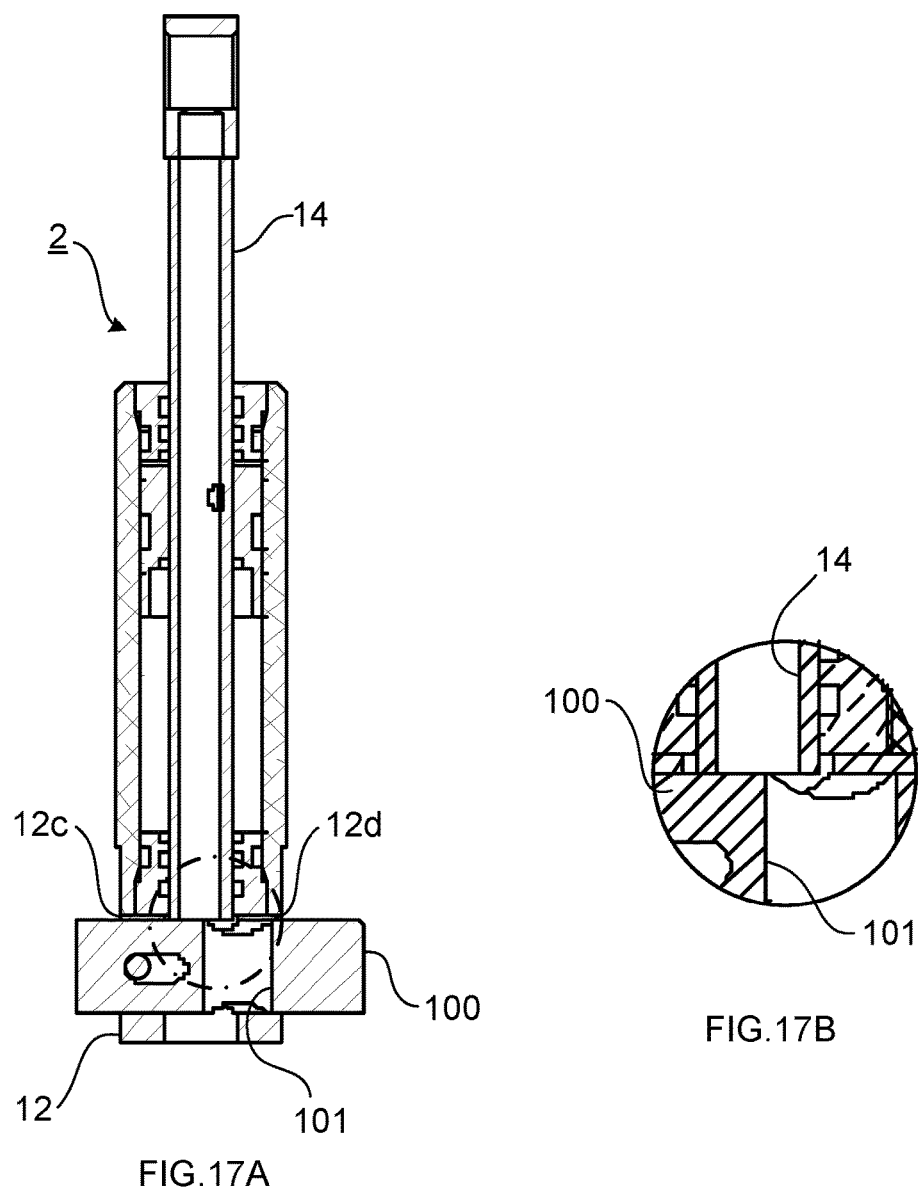
FIG. 17A is a diagram showing a configuration of a knee joint in the fourth embodiment.
FIG. 17B is an explanatory diagram of a locking mechanism in the fourth embodiment.

Next, the lock mechanism will be described with reference to FIG. 17. FIGS. 17 (A) and (B) are explanatory views of a locking mechanism, FIG. 17 (A) shows a configuration of a knee joint 2, FIG. 17 (B) shows an enlarged view of a stopper 100 portion.

As shown in FIG. 17 (A), in the locking mechanism, the end surface 12b side of the cylinder tube 12 of the knee joint 2 in the fourth embodiment, to extend the wall surface of the cylinder tube 12, two holes 12c in the wall surface, 12d are bored. Two holes 12c, 12 are drilled in opposing positions on the diameter of the bottom surface of the cylinder tube 12. Further, two holes 12c, 12d a cylindrical stopper 100 made of metal so as to penetrate is provided. The stopper 100 has a hole 101 for a diameter through which the rod 14 penetrates is drilled.

In such a locking mechanism, as shown in FIG. 17 (A), when sliding the stopper 100 to the right in the drawing, since the stopper 100 abuts against the end face of the rod 14, a locked state. Sliding the stopper 100 to the left in the figure from the locked state causes the rod 14 to penetrate the hole 101 of the stopper 100, so that the knee joint 2 is in a normal operating state (unlocked state).

Further, in the knee joint component 3 in the fourth embodiment, as shown in FIG. 16, the inlet/outlet 77 is provided in the vicinity of the inlet/outlet 74 of the cylinder tube 12. An oil passage coupled to the third oil passage 40 is provided at the front side of the orifice 40a of the third oil passage 40 from the inlet/outlet 77. This inlet/outlet 77, in a state in which the rod 14 starts to shrink from the extended state, since the hydraulic oil of the first oil chamber 13b is discharged from both the inlet/outlet 74 and the inlet/outlet 77, the hydraulic resistance is small, the rod 14 is rapidly contracted. Then, when the piston 15 reaches the position of the inlet/outlet 77, since the hydraulic oil is discharged from only the inlet/outlet 74, the hydraulic resistance is increased, the shrinkage speed of the rod 14 is reduced. In other words, the hydraulic fluid between the inlet/outlet 74 and the bottom surface of the cylinder tube 12 serves as a cushion. In the fourth embodiment, the inlet/outlet 77 is provided at a position where the bending angle of the knee joint 2 of the artificial leg 1 is 60 degrees.

According to knee joint components 3 of the fourth embodiment as described above and knee joint 2 to which it is applied, the knee joint 2 can be easily kinked to match the user's intention, made very difficult to kink, or fixed in lock state. Therefore, it is convenient for the user to use the device in the knee portion or to handle the device in the non-mounted state.

OTHER EMBODIMENTS

While embodiments of the present invention have been described above, the present invention is not limited to the present embodiment, and various forms can be taken. in the above embodiment, the oil 19 (working oil) is used as the working medium, but the working medium may be not so-called working oil but may be other liquid, or a gas such as air or nitrogen may be used as the working medium.

LIST OF REFERENCE SIGNS

Artificial leg . . . 1, Knee joint . . . 2, Knee joint component . . . 3,4,5 Thigh part . . . 7, socket . . . 8, Connecting portion . . . 8a, Bolt . . . 8b, Artificial lower leg part . . . 9, Upper lower leg . . . 9a, Hydraulic cylinder . . . 10, Cylinder tube . . . 12, End surface . . . 12a,12b, Hole . . . 12c,12d, Oil chamber . . . 13, First oil chamber . . . 13a, Second oil chamber . . . 13b, Rod . . . 14, Piston . . . 15, Ring . . . 15a,15b, Oil . . . 19, First oil passage . . . 20, Orifice . . . 20a, Check valve . . . 22, Second oil passage . . . 30, Orifice . . . 30a, Inlet/Outlet . . . 31,32, First bypass . . . 33, Orifice . . . 33a, Second bypass . . . 34, Orifice . . . 34a, Third oil passage . . . 40, Orifice . . . 40a, Switching mechanism . . . 50, First rotating member . . . 52, First rotating shaft . . . 53, Second rotating member . . . 55, Second rotating shaft . . . 56, Metal ball . . . 57, Body . . . 60, Oil chamber . . . 62, Check valve . . . 70, Inlet/Outlet . . . 74,75,76,77, Third rotating member . . . 80, Lever . . . 90, Switching valve . . . 91, Stopper . . . 100, Hole . . . 101.

The invention claimed is:

1. A knee joint component to be mounted on a hydraulic cylinder including, a cylinder tube coupled to a socket to be mounted on a thigh part, an oil chamber formed in said cylinder tube, and an oil filled in said oil chamber, and a rod coupled to an artificial lower leg part, and a piston that divides said oil chamber into a first oil chamber and a second oil chamber and that moves with the movement of said rod, the knee joint component comprising;

a first passage connecting said first oil chamber and second oil chamber, and having a first passage characteristic as said oil passes through when said piston is moving from said first oil chamber toward said second oil chamber;

a second passage arranged so as to be parallel to said first passage, and having a second passage characteristic in which a hydraulic resistance of said oil is higher than that of said first characteristic when said piston is moving from said first oil chamber toward said second oil chamber;

a third oil passage connecting said first oil chamber and said second oil chamber, and is passed through said oil when said piston is moving from said second oil chamber toward said first oil chamber;

a switching mechanism for switching whether said oil passes through either said first oil passage or said second oil passage; and said second oil passage has an inlet/outlet of said oil on the way; and said switching mechanism has a first rotating member that rotatably attaches around a first rotating shaft, and that rotates around said first rotating shaft when said artificial lower leg part is tilted, and has a second rotating member that rotatably attaches around a second rotating shaft of said first rotating member, and that rotates around said second rotating shaft when said artificial lower leg part is tilted, and that switches said oil through either said first oil passage or said second oil passage by opening or closing said inlet/outlet of said second oil passage.

2. The knee joint component according to claim 1, wherein said third oil passage has a third passage characteristic in which a hydraulic resistance of said oil is lower than that of said first characteristic and said second characteristic, and are provided with a plurality of inlet/outlet of said oil from said first oil chamber to said second oil chamber in the direction of movement of said piston in said first oil chamber.

3. A knee joint comprising; said hydraulic cylinder including, said cylinder tube coupled to said socket, and said oil chamber formed in said cylinder tube; said oil filled in said oil chamber, and said rod coupled to an artificial lower leg part, said piston that divides said oil chamber into said first oil chamber and said second oil chamber and that moves with the movement of said rod, and said knee joint component according to claim 1.

4. An artificial leg comprising; said socket mounted on a thigh, said artificial lower leg part, and said knee joint according to claim 3.

\* \* \* \* \*